(12) United States Patent
Bedenbaugh (10) Patent No.: US 7,583,999 B2
(45) Date of Patent: Sep. 1, 2009

(54) MULTI-CHANNEL CONNECTOR FOR BRAIN STIMULATION SYSTEM

(75) Inventor: Purvis Bedenbaugh, Greenville, NC (US)

(73) Assignee: Cranial Medical Systems, Inc., San Francisco, CA (US)

(*) Notice: Subject to any disclaimer, the term of this patent is extended or adjusted under 35 U.S.C. 154(b) by 0 days.

(21) Appl. No.: 11/830,565

(22) Filed: Jul. 30, 2007

(65) Prior Publication Data

US 2008/0183241 A1 Jul. 31, 2008

Related U.S. Application Data

(60) Provisional application No. 60/820,914, filed on Jul. 31, 2006.

(51) Int. Cl.
*A61N 1/36* (2006.01)
(52) U.S. Cl. .................. 607/37; 607/115; 607/116; 607/118; 439/680
(58) Field of Classification Search ............ 607/37, 607/115–116, 118
See application file for complete search history.

(56) References Cited

U.S. PATENT DOCUMENTS

| | | | |
|---|---|---|---|
| 4,236,525 A | 12/1980 | Sluetz et al. | |
| 4,437,474 A | 3/1984 | Peers-Trevarton | |
| 4,603,696 A | 8/1986 | Cross, Jr. et al. | |
| 4,736,999 A | 4/1988 | Marks et al. | |
| 4,934,366 A | 6/1990 | Truex et al. | |
| 5,906,634 A | 5/1999 | Flynn et al. | |
| 6,912,423 B2 | 6/2005 | Ley et al. | |
| 6,980,863 B2 | 12/2005 | van Venrooij et al. | |
| 2004/0039434 A1 | 2/2004 | Schrom et al. | |
| 2004/0215303 A1 | 10/2004 | Sage | |

OTHER PUBLICATIONS

International Search Report and Written Opinion of PCT Application No. PCT/US07/74876, dated Aug. 25, 2008, 7 pages total.
U.S. Appl. No. 11/828,547; filed on Jul. 26, 2007; inventor: Purvis Bedenbaugh.

*Primary Examiner*—Carl H Layno
*Assistant Examiner*—Deborah Malamud
(74) *Attorney, Agent, or Firm*—Townsend and Townsend and Crew, LLP (57) ABSTRACT

An implantable connector used with a neurological device and a lead extension includes a male connector having a plurality of electrical contacts axially arranged along the connector, insulated from each other. The connector also includes a female connector having channels axially disposed therein and a plurality of conductors axially arranged on the female connector. The plurality of conductors are electrically insulated from each other, and at least one indexing element is adjacent the channels. The indexing element allows receipt of the male connector by the channels in a defined orientation relative to the channels, thereby forming at least two electrical connections along two or more axial positions. Often the neurological device is a brain stimulating and recording lead. The male and female connectors are often fastened together with a screw or by twist-locking the two together.

44 Claims, 12 Drawing Sheets

MULTI-CHANNEL CONNECTOR FOR BRAIN STIMULATION SYSTEM

CROSS-REFERENCES TO RELATED APPLICATIONS

The present application claims the benefit of provisional U.S. Application No. 60/820,914, filed Jul. 31, 2006, the full disclosure of which is incorporated herein by reference.

BACKGROUND OF THE INVENTION

1. Field of the Invention

This invention relates generally to medical apparatus and methods, and more specifically to a connector used to electrically couple a brain stimulating and recording probe or lead to a lead extension, pulse generator or other neurological device.

Implanting medical devices such as probes or leads within the cranium is an increasingly important approach for treatment of diseases such as Parkinson's Disease, essential tremor and dystonia. Implants may be used to treat a wide array of disorders, such as depression, epilepsy, dystonia, obsessive compulsive disorder, obesity, chronic pain as well as in post-stroke rehabilitation. Most of these devices interact with the brain by applying current through an electrode. In addition, infusion of drugs through a chronically implanted probe has been proposed in the medical literature either as a primary treatment, or as an adjunctive treatment to electrical stimulation, in patients with Alzheimer's and Parkinson's Diseases, among others.

Current implantable probes are typically configured as small diameter cylinders or tubes, with several circumferential metal stimulating rings near the distal tip, and an electrically passive central axial lumen. The metal stimulating rings are used to provide electrical stimulation to tissue such as the brain, while the central axial lumen can be used to deliver the probe over a guidewire or stylet during the implantation procedure. Helical wires course through the body of the probe and terminate on another set of metal connector rings which fit into a connector integrated into a lead extension. The conductors are encased in a flexible polymer to provide insulation.

Brain stimulating and recording probes are typically connected to a lead extension through a linear array of cylindrical screw terminals. An electrical connection is made when a screw is rotated so as to impinge upon one of the stiff metal connector rings, and force it against a stranded wire which is continuous with conductors of the lead extension. The screw provides contact pressure, and under this pressure individual wire strands are slightly displaced against the surface of the stiff connector ring, providing the elements of a secure electrical connection. Flexible segments between the stiff connector rings provide mechanical isolation, so that each contact may be formed independently.

Connectors are often cylindrical with a diameter that matches the stimulating probe body and are robust enough to accommodate physical manipulation. Additionally, usually, one screw must be tightened for each electrical connection. The torque applied to the screw must be controlled carefully since over-tightening can result in damage to the screw terminal or probe, and under-tightening can result in a poor connection.

Current probe or lead designs steer electrical current into tissue by shaping the electrical field through coordinated stimulation of multiple contact sites, such as those disclosed in U.S. patent application Ser. No. 11/828,547 filed Jul. 26, 2007, the entire contents of which are incorporated herein by reference. Such probes may also record neuronal activity near stimulation sites to evaluate the state of the brain and/or disease process to evaluate the local neuronal effects of shaped electrical stimulation. Thus, more electrical contact sites are needed to integrate stimulating and recording functions, and construction of a high density multi-channel electrical connector is necessary to couple the stimulating probe with a pulse generator and controller.

For these reasons as well as others, it would be desirable to provide high density multi-channel electrical connectors for brain stimulation systems that are sterilizable, implantable and easy to use in a surgical environment. It would be particularly desirable to provide connectors which are the same diameter or smaller than the stimulating probe body. Providing small size, low profile connectors allow them to be easily implanted subcutaneously using existing surgical instruments such as guide tubes and tunnelers. It is also desirable to provide a symmetrically shaped connector so that the lead extension does not move excessively or apply excessive torque after implantation.

2. Description of Background Art

Prior patents and publications describing lead connectors include: U.S. Publication Nos. 2004/0039434 and U.S. Pat. Nos. 4,236,525; 4,437,474; 4,603,696; 6,980,863; and 6,912,423.

BRIEF SUMMARY OF THE INVENTION

The invention generally provides a connector for electrically connecting a plurality of electrical conductors. The connector is optimized to connect a neurological device such as a brain stimulating and recording lead to a lead extension or a stimulation and/or controller unit. The connector is small and suitable for implantation into the body. Its shape and configuration facilitates convenient handling by surgeons and other healthcare professionals in the operating room. Its size minimizes the metal required to make electrical connections, which in turn improves compatibility with imaging systems which depend on magnetic fields, such as magnetic resonance imaging (MRI), spectroscopy, and magneto encephalography (MEG).

In a first aspect of the present invention, a connector for coupling a neurological device with a lead extension comprises a male connector having a plurality of electrical contacts axially arranged along the connector and electrically insulated from each other. The connector also includes a female connector having one or more channels axially disposed therein and a plurality of conductors axially arranged thereon. The plurality of conductors are electrically insulated from each other. Also, at least one indexing element is disposed adjacent to one or more of the channels and the indexing element allows the male connector to be received into the one or more channels in a defined orientation relative to the channel, thereby forming at least two electrical connections along two or more axial positions.

In a second aspect of the present invention, a connector system comprises a connector comprising a male connector, a female connector, and one or more channels axially disposed in the female connector, wherein at least one of the channels has an indexing element adapted to receive the male connector in a defined orientation relative to the female connector, thereby forming at least two electrical connections along two or more axial positions. The system also includes a neurological device that is electrically coupled with at least one of the male and female connectors and a lead extension also electrically coupled with at least one of the male and female connectors. An implantable and controllable pulse generator is also included in the system. The pulse generator is adapted to provide an electrical stimulus to the neurological device via the male and female connectors. The system may include a protective sheath that is adapted to cover the male and female connectors as well as an anchoring device. The anchoring device is adapted to removably fix the neurological device to a patient's head. Sometimes the system may include a patient programmer that is adapted to control the pulse generator.

In a third aspect of the present invention, a method for connecting a neurological device with a lead extension comprises positioning a male connector relative to a female connector having one or more channels disposed therein and inserting the male connector into one of the channels thereby forming at least two electrical connections along two or more axial positions. The male and female connectors are releasably fastened together and then the coupled male and female connectors are implanted into a patient. The step of fastening may comprise tightening a screw and also the step may comprise rotating the male connector relative to the female connector thereby forming a secure electrical connection therebetween.

The male connector may be electrically coupled with a neurological device such as a brain stimulating and recording lead. The female connector may be electrically coupled with a lead extension or other medical device. Sometimes the female connector and the lead extension are fixedly coupled together or they may be integral with one another. Sometimes at least some of the conductors of the female connector are integral with wires in the lead extension. Often, the male and female connectors are compatible with magnetic resonance imaging. Also, when the male and female connectors are engaged together they may form a hermetic seal or be wrapped by a sheath which forms the seal. The sheath usually covers at least a portion of the male and female connectors.

Sometimes the male connector comprises two or more elongated members. At least one of these elongated members may be hemi-cylindrically shaped or the male connector may have a cross-sectional shape selected from the group consisting of rectangular, triangular, elliptical, circular, square and ovoid. Often the female connector has a longitudinal axis and the at least two electrical connections are symmetrical thereabout. The female connector may slidably receive the male connector.

Sometimes the male connector may comprise a rod receivable by the channel and wherein the plurality of electrical contacts are disposed on tabs radially extending outward from the rod, thus the male connector rotationally engages the female connector. Two or more tabs may be disposed circumferentially around the rod at two or more axial positions, with each tab having at least two electrical contacts. Sometimes, the rod comprises a central cavity through which electrical conductors from the neurological device traverse at least partially and the electrical conductors may terminate at electrical contacts disposed on the tabs. The tabs may be spaced apart by valleys through which electrical conductors from the neurological device traverse. Sometimes the conductors comprise spring terminals and the spring terminals may follow a substantially helical path along a longitudinal axis of the female connector, forming a cardiod shape when viewed from an end of the female connector.

The connector may also comprise a fastener adapted to releasably compress at least two of the conductors in the female connector against at least two of the contacts in the male connector thereby forming at least two secure electrical connections therebetween. Sometimes the fastener comprises a screw that is threadably engaged with the female connector. Sometimes the connector may comprise a rotating camshaft or a plug slidably received by the female connector. The camshaft or plug is adapted to releasably compress at least two of the conductors in the female connector against at least two of the contacts in the male connector thereby forming at least two secure electrical connections therebetween.

The male connector may engage the female connector forming a body with a profile that is substantially cylindrical such that when the body is rotated it has substantially the same profile in any position. The male connector may comprise a polymer selected from the group consisting of polyetheretherketone (PEEK), polyetherimide (Ultem™) and polyimide. Also, the indexing element may be integral with the female connector and it may be a pin. Sometimes the connector may have a central lumen that is adapted to accommodate a guidewire, stylet or fluid. The female connector may be of monolithic construction and it may comprise a polymer selected from the group consisting of polyetheretherketone, polyetherimide and polyimide. The female connector may also be fabricated substantially from a metal such as stainless steel. Sometimes the female connector comprises a dividing element separating two axial groups of conductors with the plurality of contacts and disposed in the dividing element.

The plurality of conductors may comprise a conductor selected from the group consisting of thin film conductors, thick film conductors, wire conductors and printed circuit conductors. The connector may also comprise a cassette, wherein the male connector is received in the cassette and the cassette is received in the female connector. Also included is a cassette fastener which is adapted to releasably couple the cassette, the male connector and the female connector together. The cassette fastener may threadably couple the cassette, the male connector and the female connector together. The connector may also comprise a bump stop which is adapted to help align the male connector with the female connector and also to prevent the male connector from moving in at least one direction relative to the female connector. The connector also may include a protective sheath adapted to cover the male and female connectors.

These and other embodiments are described in further details in the following description related to the appended drawing figures.

DETAILED DESCRIPTION OF THE INVENTION

Figures 1, 2:
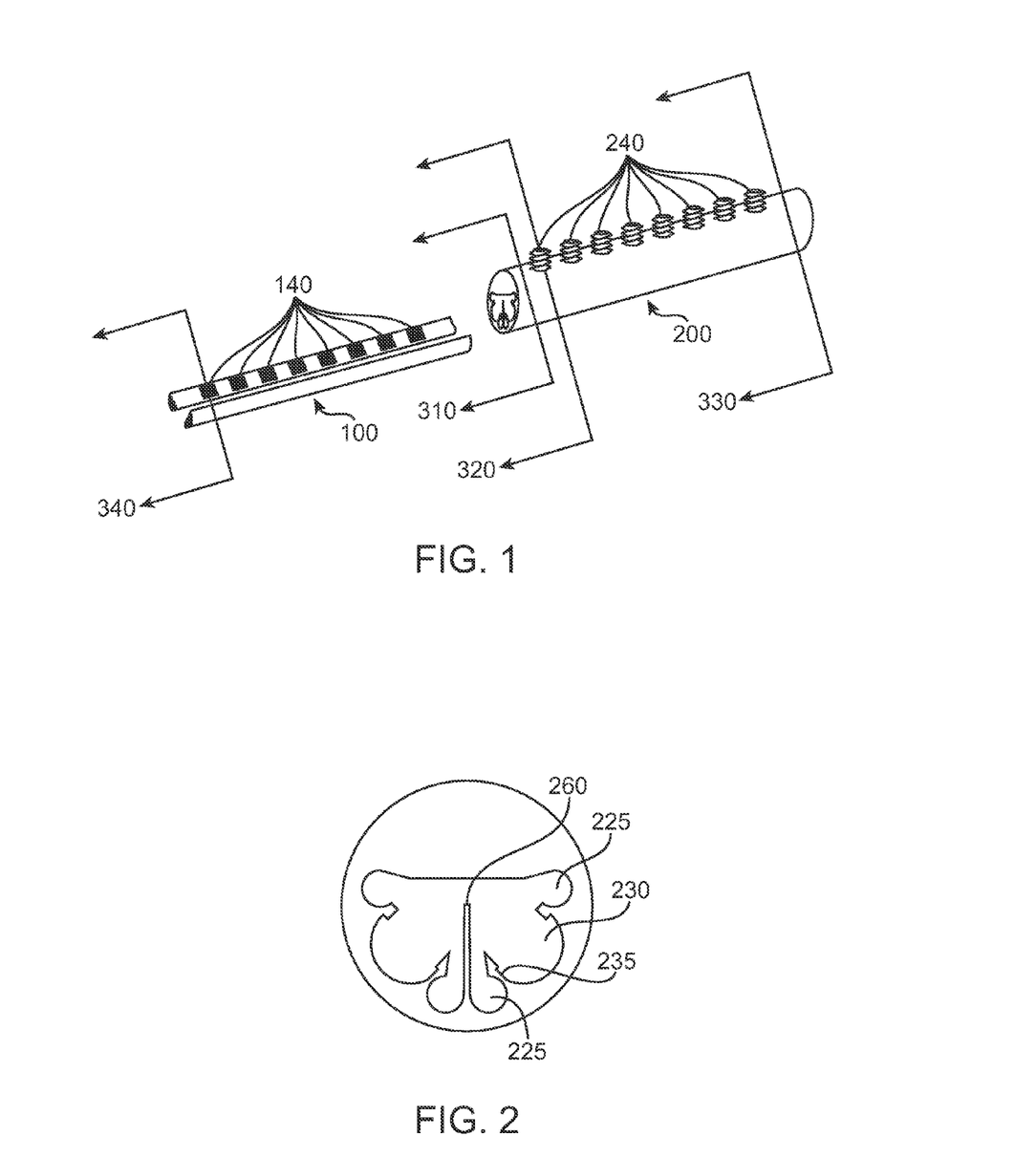
FIG. 1 shows an embodiment of a multi-channel connector.
FIG. 2 illustrates a cross-section of the embodiment shown in FIG. 1.

FIG. 1 illustrates a preferred embodiment of the present invention. A multiple contact connecting terminal, also referred to as a male connector 100 is integrated with a brain stimulating and recording probe. It is comprised of two hemi-cylindrical contact strips, each with a linear array of electrical contacts 140. The hemi-cylindrical strips 100 insert into a cylindrical multiple contact connecting terminal also referred to as a female connector 200 integrated with a lead extension. Screws 240 provide pressure to ensure secure electrical connections.

Figure 8:
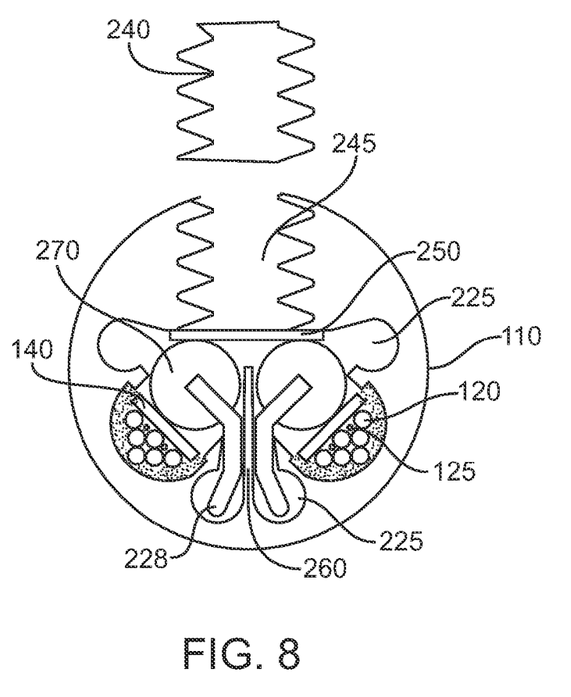
FIG. 8 illustrates a cross-section of an assembled multi-channel connector.

FIG. 2 illustrates a cross-section at position 310 of the embodiment illustrated in FIG. 1. This part could be manufactured by extrusion, or it could be machined. The probe terminal strips 100 slide into cavities or channels 230, and are indexed by the flat surface 235. In alternative embodiments the space 235 could be a hemi-cylinder, and a small wire, rod or flat insert could index the terminal strips 100 to ensure that each strip can be inserted into one cavity. Such inserts need not course the entire length of the connecting terminal 200, but could course only a limited axial distance in the vicinity of cross section 330. It could also have a taper at its distal end, to facilitate insertion and proper seating of the terminal strips 100, in the manner of a chamfer. The dividing wall 260 separates and electrically insulates compressible contacts 270 (FIG. 8). It may be an integrated feature of the lead extension terminal 100, or it may be a separate part. Lead extension wires course through the cavities 225 at more proximal stations.

Figure 3:
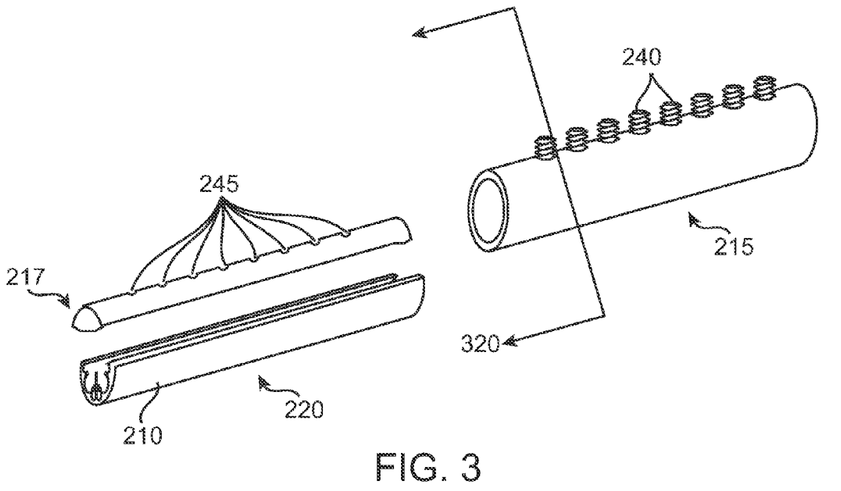
FIG. 3 illustrates another embodiment of a multi-channel connector.

FIG. 3 illustrates an alternative embodiment of the lead extension terminal, in which a positioning cassette 220 inserts into the cylindrical terminal body 215. This embodiment facilitates fabrication by machining. A spacer 217 positions the cassette 210 properly within the cylinder. Holes 245 permit screws 240 to travel through the spacer 217 to press upon the internal parts and effect a secure electrical connection. The body 215 is a cylinder. During manufacturing, the spacer 217 and cassette 220 may be inserted into the body 215 before drilling and tapping the holes 245, at which time the spacer 217 may be permanently attached to the body 215 by an adhesive. The cylindrical terminal body 215 may be made of an engineered plastic, or for extra strength may be made of a metal such as stainless steel, MP35N or other cobalt-chrome alloy, or tungsten. In one particular embodiment, the cylindrical terminal body is a 6 or 7 gauge thin-walled stainless steel hypodermic tube.

Figure 4:
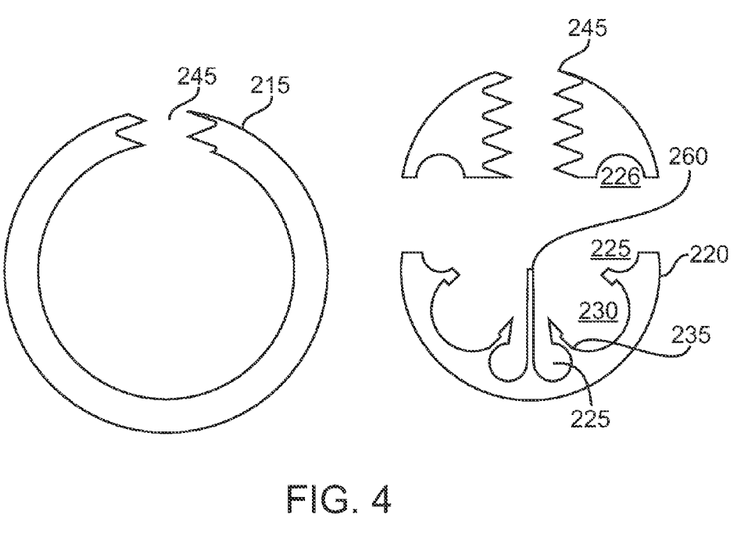
FIG. 4 illustrates a cross-section of the embodiment shown in FIG. 3.

FIG. 4 provides an enlarged cross-sectional view of each of the major components of the embodiment in FIG. 3. The probe terminal strips 100 slide into the cavities 230, indexed by a flat surface 235. As in the embodiment of FIG. 2, in variations of this embodiment space 235 could be a hemi-cylinder, and a small wire, rod or flat insert could index the terminal strips 100 to ensure that each strip can be inserted into one cavity. Such inserts need not course the entire length of the connecting terminal 220, but could course only a limited axial distance in the vicinity of cross section 330. It could also have a taper at its distal end, to facilitate insertion and proper seating of the terminal strips 100, in the manner of a chamfer. Wires integrated with the lead extension course through the spaces 225 and 226. In this embodiment the spaces 226 in the spacer 217 may be machined by a larger tool than the spaces 225, to facilitate insertion of the assembled cassette into the connector body 215 with the lid of the cassette 217 pre-attached. Holes 245 are adapted to receive screws 240.

Figure 5:
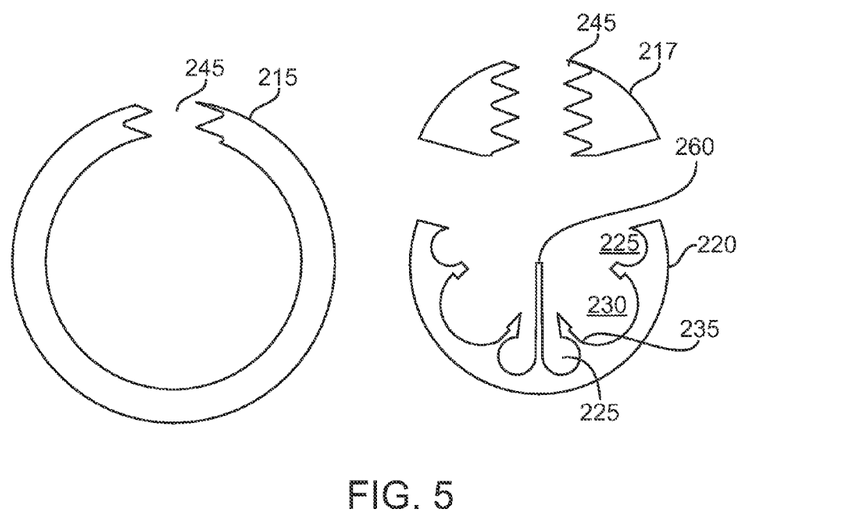
FIG. 5 illustrates still another embodiment of a multi-channel connector.

FIG. 5 illustrates an alternative cassette based embodiment, where the spaces 225 for the lead extension wires lay entirely within the cassette 220. FIGS. 4-5 illustrate how different embodiments of the invention can present different manufacturing challenges. For example, if the embodiment of FIG. 4 is machined, the lower surface can be fabricated by a single flat cut, followed by machining two channels 226. The embodiment of FIG. 5, on the other hand, requires three precise flat cuts.

Figure 6:
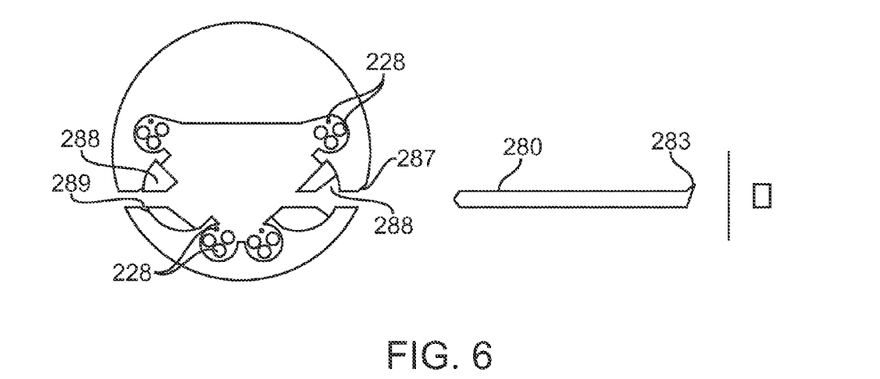
FIG. 6 illustrates the use of an alignment pin for proper indexing of connector components.

FIG. 6 illustrates the position of an alignment pin in the embodiments of FIGS. 1 and 3, at section 330. The terminal strips 100 are first positioned into nearly correct alignment by pushing against the end of the lead extension terminal body 210 or 215. Then a single pin 280 is inserted through the lead extension terminal body and the two terminal strips. The pin 280 may be angled or chamfered to facilitate insertion, and the receiving surfaces 287, 288, 289 are also chamfered or beveled to facilitate final alignment by the pin. In alternative embodiments the receiving surfaces need not be beveled. The stop flare 283 may fit flush against the receiving surface 287, and may be shaped by forging.

Figure 6A:
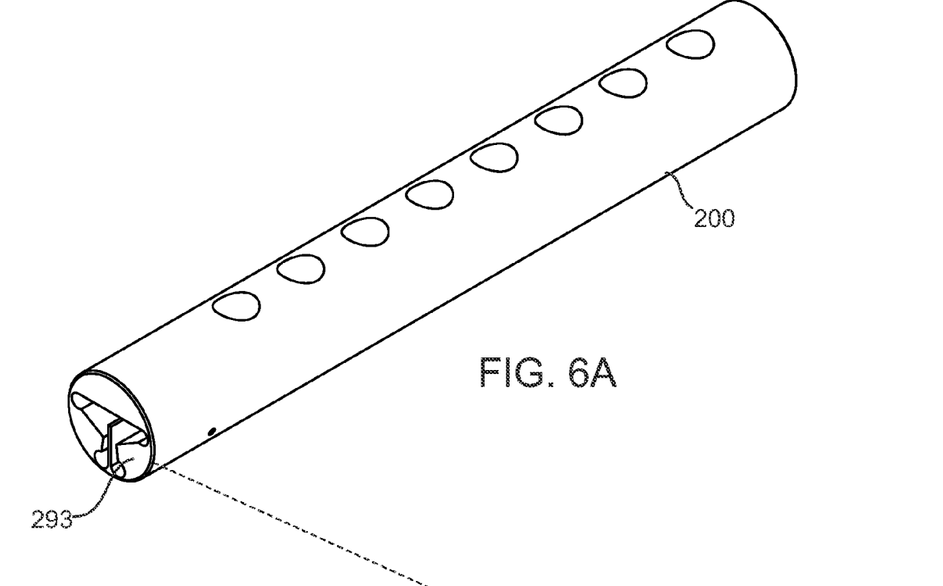
FIG. 6A shows a perspective view of an exemplary embodiment of a connector.
Figures 6B, 6C, 6D:
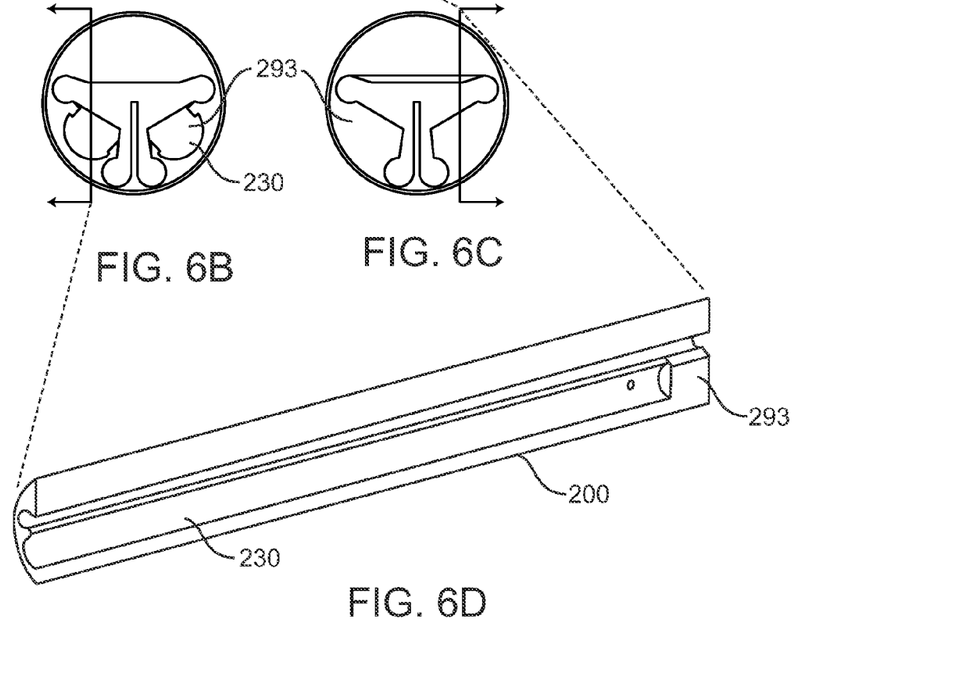
FIG. 6B shows a front end view of the connector in FIG. 6A.
FIG. 6C shows a back end view of the connector in FIG. 6A.
FIG. 6D shows a longitudinal cross section of the connector in FIG. 6A.

FIGS. 6A-6D illustrate an embodiment which incorporates a bump-stop 293, a mechanical feature which facilitates course alignment of the contact strips with contact pads, to facilitate insertion of the pin 280. The pin 280 ensures fine alignment. FIG. 6A shows a perspective view of the connector, with the back end, showing the bump-stop 293 in the foreground. FIG. 6B shows an end view of the front of the connector, with receiving cavities or channels 230 terminated with the bump-stop 293. FIG. 6C shows an end view of the back of the connector, with the bump-stop 293 obscuring the view of the receiving cavities or channels 230. FIG. 6D shows a cross-section view showing the receiving cavity or channel 230 terminated by the bump-stop 293.

Figure 7:
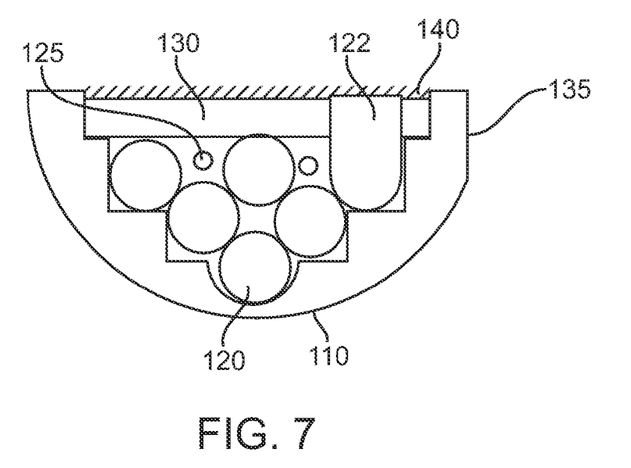
FIG. 7 illustrates a cross-section of the multi-contact terminal portion of the embodiment shown in FIG. 1.
Figure 18A:
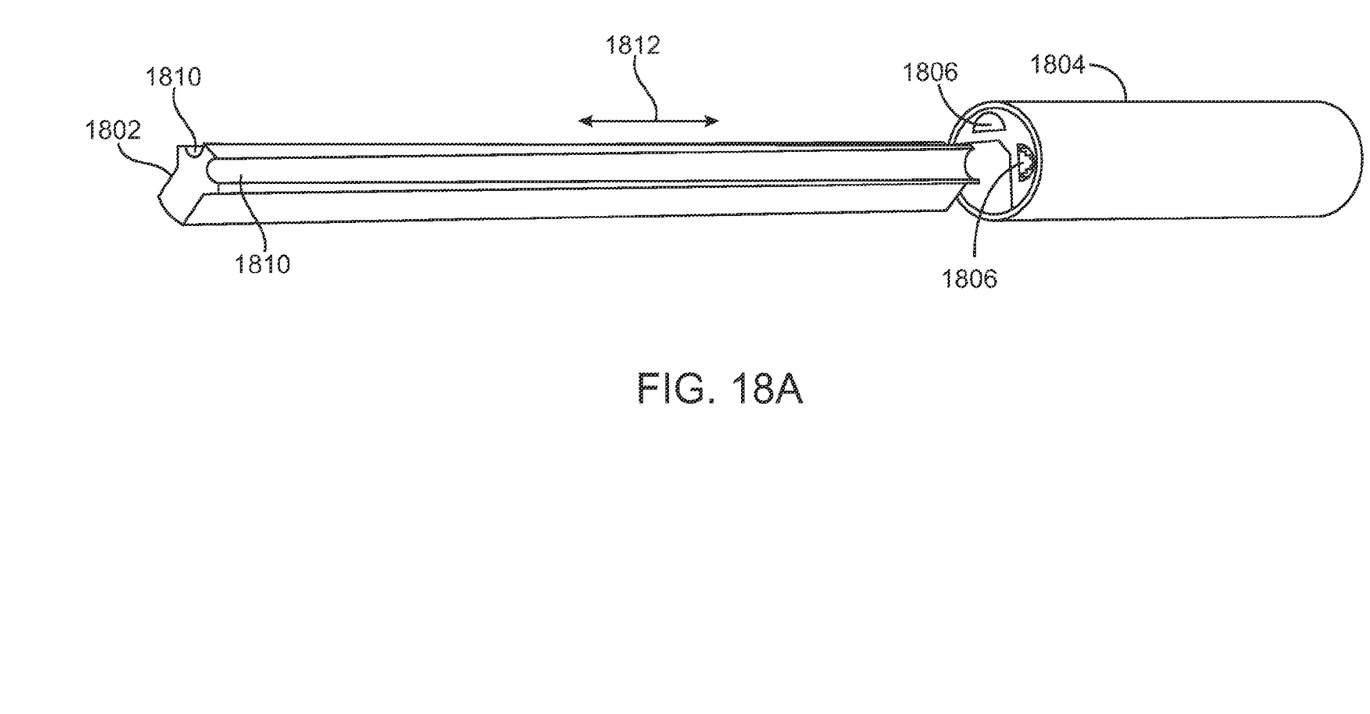
FIGS. 18A-18B illustrate the use of plug to form electrical contacts between the male and female connectors.
Figure 18B:
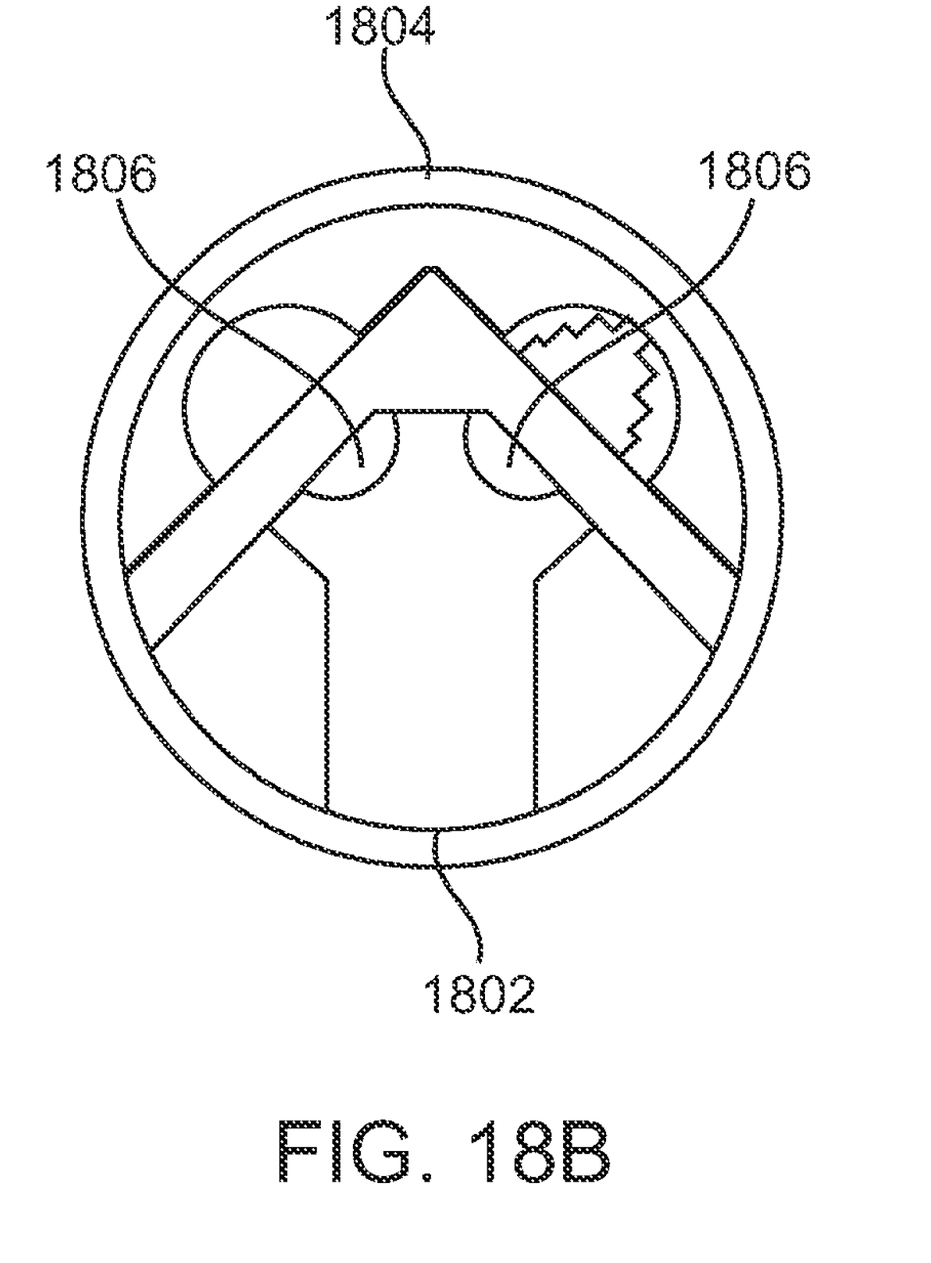

FIG. 7 illustrates a cross-section of the probe terminal 100 in the embodiment of FIGS. 1 and 3, including the conductors 120, 125, and the terminal strip 130. The terminal strip provides a firm surface to support the electrical contact 140 as the compressible contact 270 (FIG. 8) is forced against it by the screw 240 and pressure plate 250. At each electrical contact, one conductor from the probe penetrates the terminal strip 130 to make a connection with the electrical contact. For example, stimulating conductor 120 contacts with electrical contact 140 at position 122. The connection can be made by welding, or by thin film metallization. The profile of the terminal shell 110 can be thicker in later cross-sections, as wires terminate. In alternative embodiments, the key surface 135 may only be at the end of the probe terminal, beyond the alignment pin. In alternative embodiments, a divot in the terminal strip 130 accommodates a guidewire when two terminal strips appose each other. In other embodiments, the flat surface 135 may extend for the length of the terminal 100, and a guidewire may course alongside the apposed strips, and be channeled to the center of the stimulating and recording probe past the point where electrical connections are made. In some alternative embodiments, the pressure plate 250 can be forced against the compressible contacts 270 by a plug as illustrated in FIGS. 18A-18B. FIG. 18A shows a perspective view of plug 1802 which is slidably received axially in the direction of arrow 1812 into female connector 1804 having channels 1806 which receive the male connector. Plug 1802 also has channels 1810 which provide space for conductor wires. FIG. 18B shows a side view of FIG. 18A. In still other embodiments, a rotating camshaft may be used instead of the plug.

In alternative embodiments, the connecting terminal integrated with the brain stimulating and recording probe could be constructed with printed circuit or flexible circuit technology. For example, two planar multilayer printed circuits could be apposed to each other, and ground or machined into a cylinder of the appropriate diameter so that the contact an fit inside of a stylet when integrated with a medical lead. In alternative embodiments, the shape need not be a hemi-cylinder, and may be flat, rectangular, triangular, elliptical, circular, square or ovoid in cross-section, although such embodiments may be incompatible with existing surgical instruments such as a probe insertion guide tube.

FIG. 8 illustrates a cross-section through the assembled connector. Each screw secures two electrical connections. Engineered plastics such as PEEK, Ultem and/or Kapton ensure high strength and close tolerances between the parts. The compressible contacts 270 accommodate variations in the precise distances between parts, as well as insuring that microscopic displacement can occur between conductors in contact with each other. When the screw 240 impinges upon the pressure plate, compressible contacts 270 are forced against the electrical contacts 140. As the contacts compress, at the micro level, the conductive surfaces are displaced against each other and plastically deformed, ensuring a secure electrical connection. In different embodiments of the invention, the compressible contacts could be a modified twist pin, a fuzz button, a short rod, tube, or block of conductive elastomer, or other compressible conductor known to those skilled in the art. The orientation of the flat electrical contacts 140 is approximately 45° relative to the direction of the force generated by the screw 240, to ensure stable positioning of the compressible contacts 270. A barrier wall 260 insulates the compressible contacts from each other, and is of a height which provides electrical insulation, while not interfering with the downward displacement of the pressure plate 250. At each screw position, each of two lead extension wires is integrated into a compressible contact.

In alternative embodiments, the dividing wall could be a thin multilayer circuit board, circuit card or flexible circuit, with conducting pads along the upper most portion, and conductors along the lower portion and within the inner layers. In such embodiments, the upper cavities for lead extension wires 225 would not be needed, and the lower cavities for lead extension wires could assume the form of a slot positioning the dividing wall 260.

Figure 9:
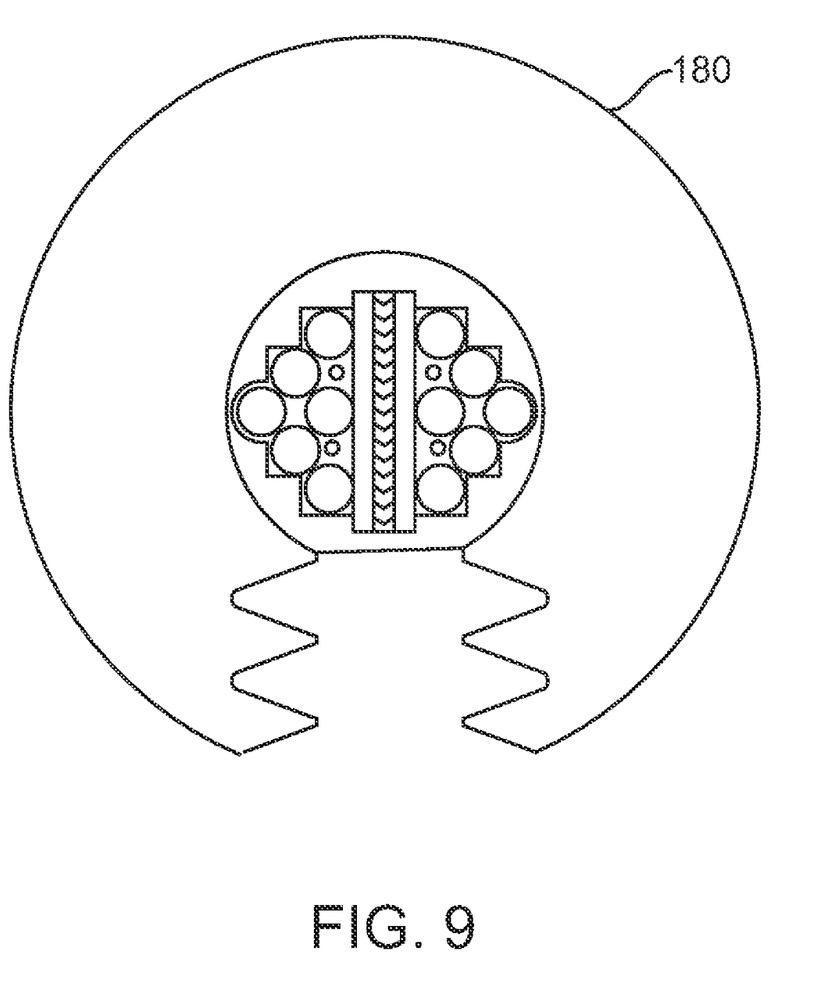
FIG. 9 illustrates a protective sheath used for handling the multi-contact terminal.

FIG. 9 illustrates a protective cover 180 for easy handling of the multiple contact connecting terminal integrated with the brain stimulating and recording probe 100. It is a cylinder, with a central cavity sized to receive the two branches of the connecting terminal apposed to each other. In the embodiment illustrated, a single set screw captures the terminal inside the cylinder. In an alternative embodiment, a pin similar to that illustrated in FIG. 6, but with a head that facilitates quick and easy removal. Such a pin could take the form of a loop of fine wire, such as a fine wire suture, which could be twisted to temporarily capture the terminal within the cover. In an alternative embodiment, the protective cover may be a thin elastomeric sheet.

Figure 10:
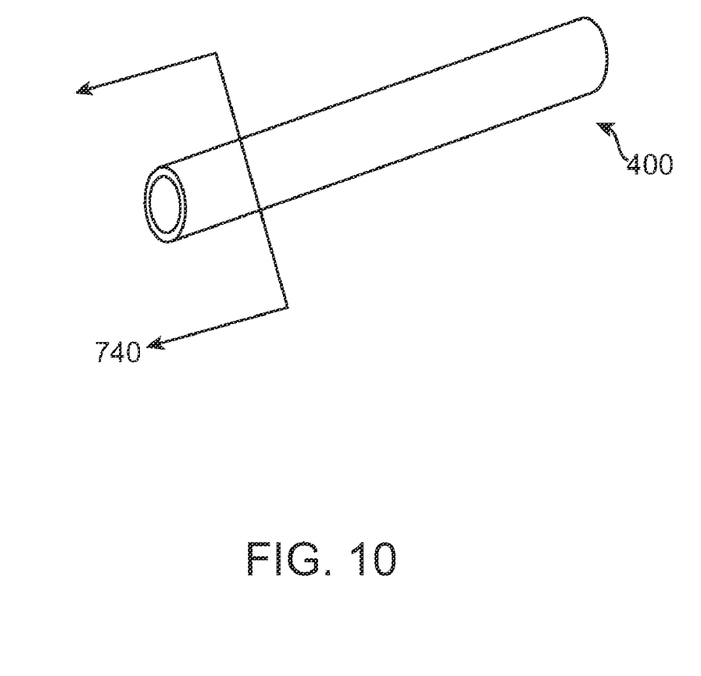
FIG. 10 illustrates another embodiment of a multi-channel connector.

FIG. 10 illustrates an alternative embodiment of the invention, in which connecting contacts are made by a twist action. A multiple contacting connecting terminal 500 at the end of the brain stimulating and recording probe inserts into a multiple contact connecting terminal at the end of the lead extension. Up to 8 electrical contacts appear on projecting surfaces of each multi-contact tab 520. An electrical connection is made when the probe terminal 500 is twisted, wiping electrical contacts on the tabs 520 against helical spring contacts within the body of the lead extension terminal 400. Connecting terminal 500 has two contact tabs 520 while connecting terminal 501 has three contact tabs 520.

Figure 11A:
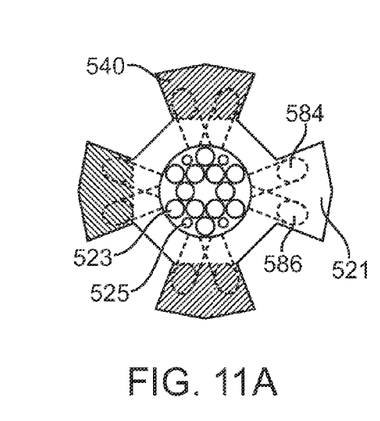
FIGS. 11A-11B illustrate the connecting tabs in the embodiment of FIG. 10.
Figure 11B:
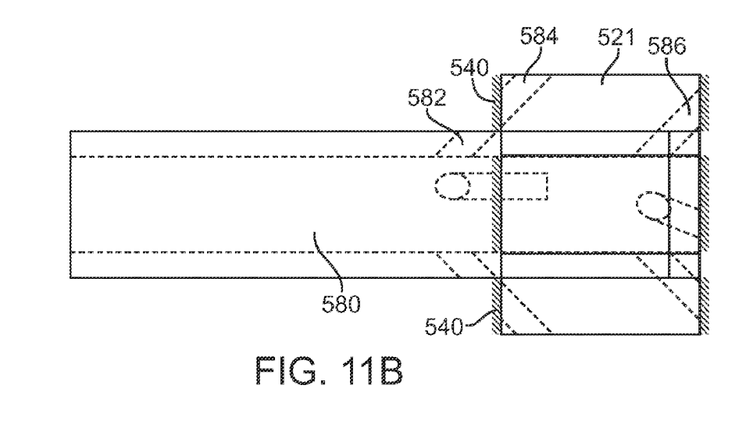

FIGS. 11A-11B illustrate an embodiment of the connecting tabs 520 of the connector embodiment of FIG. 10. FIG. 11A highlights tabs 521 and FIG. 11B is a side view of the connector. Four tabs 521 extend from the shaft. Two electrical contacts 540 appear on each tab, one facing towards the opening of the lead extension terminal 400, and one facing away from the opening. In the axial view, the electrical contact 540 is omitted from one tab for clarity. Likewise for clarity, the back tab is omitted from the parasaggital view. Stimulating 523 and recording 525 wires course through a central cavity 580 and exit to achieve continuity with the electrical contacts 540. The vias 582, 586 are angled in the same direction, to facilitate fabrication of the probe terminal as a monolithic part, with the conductors threaded into the terminal. Other embodiments may include a cavity 590 to accommodate a guidewire, as seen in FIG. 12.

Those skilled in the art will recognize that such a shape can be constructed through machining, which will generate an extra hole 584, as a byproduct of the fabrication process. One way to machine such a part is to use a lathe to bore the central cavity 580 in a rod. Next, grooves are machined into the rod at the points where the multi-tab terminals 520 will be placed, with the deepest part of the grove at the outer extent of the tabs, and the sides of the groove orthogonal to the axis of the vias 582. Additional grooves are machined with sides orthogonal to the vias 586. A drill is used to form the holes which become the vias 582 and the accessory holes 584, as well as the holes which become the other vias 586. On the lathe, the material between the tab faces and beyond the extent of the tabs is removed.

Figure 12:
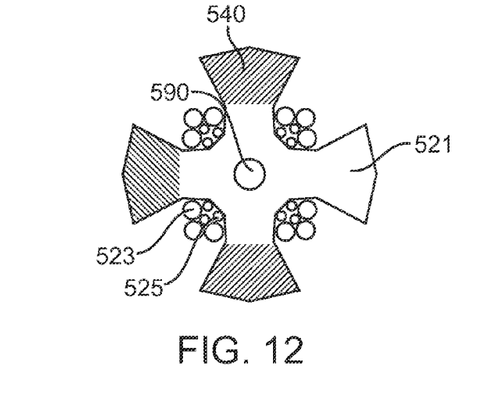
FIG. 12 illustrates another embodiment of the connecting tabs in the embodiment of FIG. 10.

FIG. 12 illustrates an alternative embodiment of the multiple tab terminals 521, in which the probe conductors course outside of the terminal body. This embodiment has the advantage of simpler fabrication compared to the embodiment in FIGS. 11A-11B. It has the disadvantage of being weaker compared to the embodiment of FIG. 11, because the material forming the shaft of the terminal is placed closer to the center of the shaft. A central cavity 590 can accommodate a guidewire or fluid. Again, the electrical contact 540 has been omitted from one of the tabs 521 so that the tab may be clearly labeled.

Figure 13A:
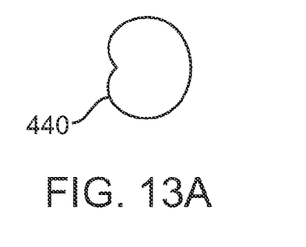
FIGS. 13A-13B illustrate the shape of helical cardioid spring contacts.

FIG. 13A illustrates the basic shape of the helical cardioid spring contacts 440 of the extension lead terminal. Electrical contact is made when the probe terminal shaft is rotated, so that the flat electrical contacts 540 are wiped against these spring contacts. These contacts may be constructed of a conventional material. An example of a conventional material is an alloy of beryllium and copper, with the possible addition of nickel and cobalt. They may also be made of a biocompatible material, and may be gold plated.

Figure 13B:
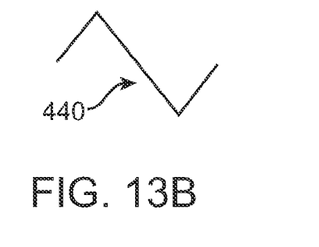
Figure 14:
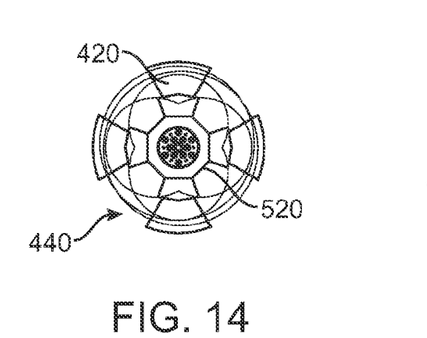
FIGS. 14 and 15 illustrate how connecting tabs engage cardioid spring contacts.
Figure 15:
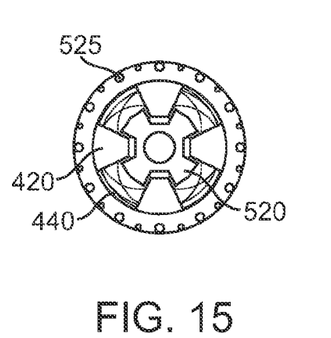
Figure 16A:
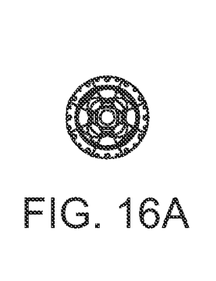
FIGS. 16A-16B illustrate the multi-channel connector of FIG. 10 assembled.
Figure 16B:
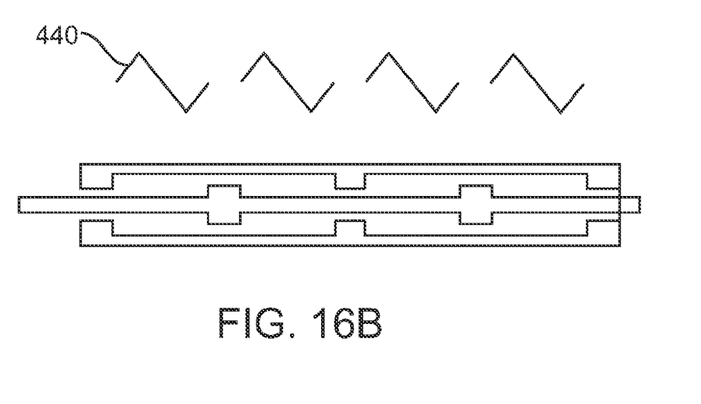

FIGS. 14 and 15 illustrate some of the special advantages of such a shape. Four such springs are oriented along equally spaced angular directions, and press against each face of each multiple contact tab 520. The ends of the spring are closer to the center of the connector. One end is fixed in a support tab 420, and the other scrapes against the contact 540. FIG. 13B illustrates the configuration in which the contacts are engaged. FIG. 14 illustrates the configuration in which the contacts are not engaged, and the individual tabs probe contact tabs 521 can slide through the spaces between the springs as the probe terminal is inserted into the lead extension terminal. FIGS. 16A-16B show an end view and side view of the components of the multi-channel connector FIG. 10 assembled.

Figure 17:
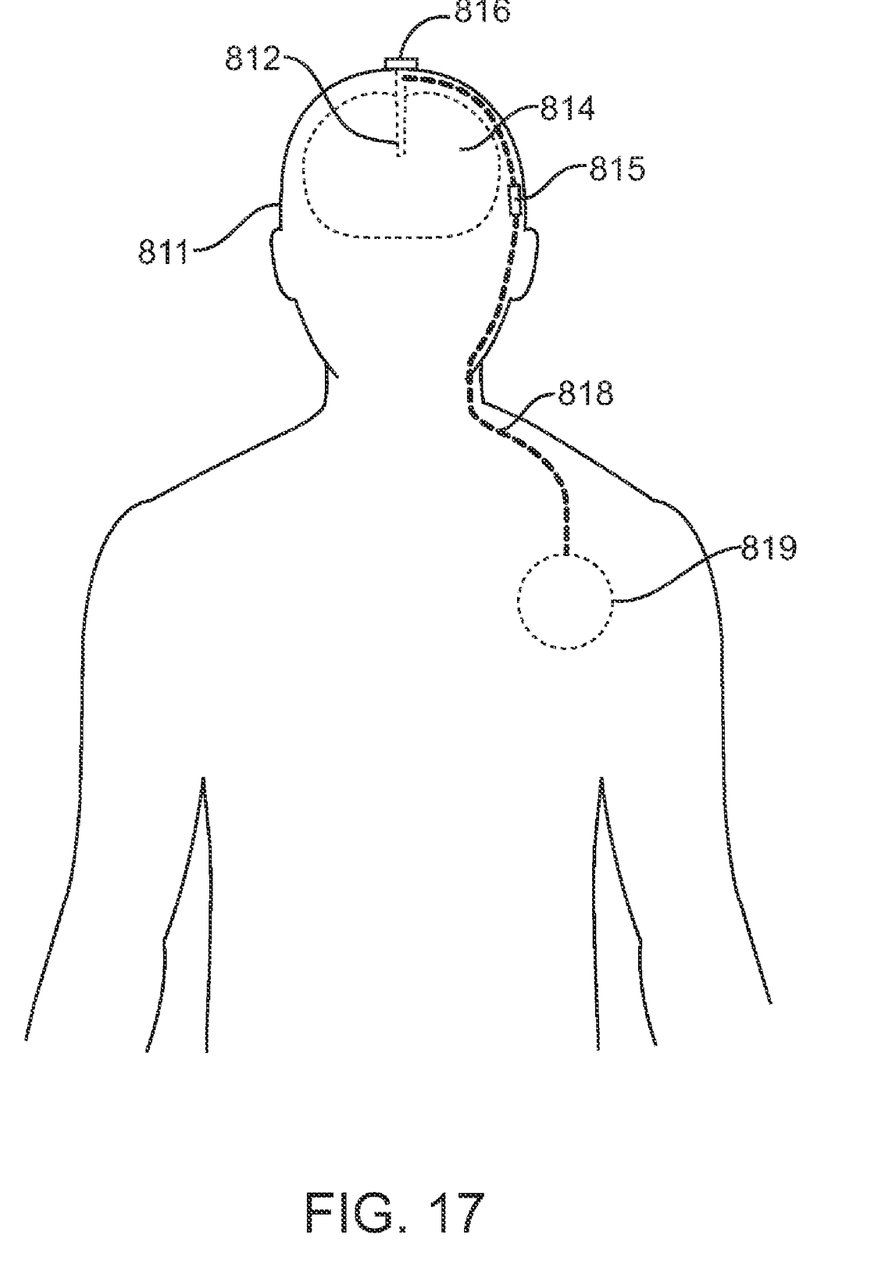
FIG. 17 shows a brain stimulating and recording lead implanted in a patient.

FIG. 17 shows a monitoring and modulating probe or lead 812 secured to the skull 811 of a patient with a fixture 816 and implanted into brain tissue 814. An extension lead 818 couples the probe 812 with a controllable pulse generator 819 via connector 815. Connector 815 comprises a male and female connector coupled together. The lead often runs under the patient's skin, although it may not and the controllable pulse generator 819 may be implanted or it may remain external to the body of the patient. Additional details on a fixture for securing the probe to the skull are disclosed in U.S. Provisional Patent Application No. 60/908,367 filed Mar. 27, 2007, the entire contents of which are incorporated herein by reference.

While the exemplary embodiments have been described in some detail for clarity of understanding and by way of example, a variety of additional modifications, adaptations and changes may be clear to those of skill in the art. Hence, the scope of the present invention is limited solely by the appended claims.

What is claimed is:

1. A connector for coupling a neurological device with a lead extension, the connector comprising:
   a male connector having a plurality of electrical contacts axially arranged along the connector and electrically insulated from each other;
   a female connector having one or more channels axially disposed therein and a plurality of conductors axially arranged thereon, the plurality of conductors electrically insulated from each other; and
   at least one indexing element disposed adjacent to one or more of the channels,
   wherein the at least one indexing element allows the male connector to be received into the one or more channels in a defined orientation relative to the channel,
   thereby forming at least two electrical connections along two or more axial positions, and
   wherein the male connector is electrically coupled with the neurological device, the neurological device comprising a brain stimulating and recording lead.

2. A connector as in claim 1, wherein the male and female connectors form a hermetic seal when engaged together.

3. A connector as in claim 1, further comprising a sheath that is adapted to cover at least a portion of the male and female connectors thereby forming a hermetic seal therebetween.

4. A connector as in claim 1, wherein the female connector is electrically coupled with a lead extension.

5. A connector as in claim 4, wherein the female connector and the lead extension are fixedly coupled together.

6. A connector as in claim 4, wherein the female connector is integral with the lead extension.

7. A connector as in claim 4, wherein at least some of the conductors of the female connector are integral with wires in the lead extension.

8. A connector as in claim 1, wherein the male and female connectors are compatible with magnetic resonance imaging.

9. A connector as in claim 1, wherein the male connector comprises two or more elongated members.

10. A connector as in claim 1, wherein at least one of the elongated members is substantially hemi-cylindrically shaped.

11. A connector as in claim 1, wherein the male connector has a cross-sectional shape selected from the group consisting of rectangular, triangular, elliptical, circular, square and ovoid.

12. A connector as in claim 1, wherein the female connector has a longitudinal axis and the at least two electrical connections are symmetrical thereabout.

13. A connector as in claim 1, wherein the female connector slidably receives the male connector.

14. A connector as in claim 1, further comprising a fastener adapted to releasably compress at least two of the conductors in the female connector against at least two of the contacts in the male connector thereby forming at least two secure electrical connections therebetween.

15. A connector as in claim 14, wherein the fastener comprises a screw threadably engaged with the female connector.

16. A connector as in claim 1, further comprising a rotating camshaft adapted to releasably compress at least two of the conductors in the female connector against at least two of the contacts in the male connector thereby forming at least two secure electrical connections therebetween.

17. A connector as in claim 1, further comprising a plug slidably received by the female connector and adapted to releasably compress at least two of the conductors in the female connector against at least two of the contacts in the male connector thereby forming at least two secure electrical connections therebetween.

18. A connector as in claim 1, wherein the male connector comprises a rod receivable by the channel and wherein the plurality of electrical contacts are disposed on tabs radially extending outward from the rod.

19. A connector as in claim 18, wherein the male connector rotationally engages with the female connector.

20. A connector as in claim 18, wherein two or more tabs are disposed circumferentially around the rod at two or more axial positions, with each tab having at least two electrical contacts.

21. A connector as in claim 18, wherein the rod comprises a central cavity through which electrical conductors from the neurological device traverse at least partially.

22. A connector as in claim 21, wherein the electrical conductors terminate at electrical contacts disposed on the tabs.

23. A connector as in claim 18, wherein the tabs are spaced apart by valleys through which electrical conductors from the neurological device traverse.

24. A connector as in claim 18, wherein the conductors comprise spring terminals.

25. A connector as in claim 24, wherein the spring terminals follow a substantially helical path along a longitudinal axis of the female connector, forming a cardiod shape when viewed from an end of the female connector.

26. A connector as in claim 1, wherein the male connector engages the female connector forming a body with a profile that is substantially cylindrical such that when the body is rotated it has substantially the same profile in any position.

27. A connector as in claim 1, wherein the indexing element is integral with the female connector.

28. A connector as in claim 1, wherein the indexing element is a pin.

29. A connector as in claim 1, further comprising a central lumen adapted to accommodate a guidewire or stylet.

30. A connector as in claim 1, further comprising a central lumen adapted to accommodate fluid.

31. A connector as in claim 1, wherein the female connector is of monolithic construction.

32. A connector as in claim 1, wherein the male connector comprises a polymer selected from the group consisting of polyetheretherketone, polyetherimide and polyimide.

33. A connector as in claim 1, wherein the female connector comprises a polymer selected from the group consisting of polyetheretherketone, polyetherimide and polyimide.

34. A connector as in claim 1, wherein the female connector is fabricated substantially from a metal.

35. A connector as in claim 34, wherein the metal is stainless steel.

36. A connector as in claim 1, wherein the plurality of conductors comprise a conductor selected from the group consisting of thin film conductors, thick film conductors, wire conductors and printed circuit conductors.

37. A connector as in claim 1, wherein the female connector comprises a dividing element separating two axial groups of conductors and wherein the plurality of contacts and are disposed in the dividing element.

38. A connector as in claim 1, further comprising:
 a cassette, wherein the male connector is received in the cassette and the cassette is received in the female connector; and
 a cassette fastener, the cassette fastener adapted to releasably couple the cassette, the male connector and the female connector together.

39. A connector as in claim 38, wherein the cassette fastener threadably couples the cassette, the male connector and the female connector together.

40. A connector as in claim 1, wherein the female connector comprises a bump stop, the bump stop adapted to help align the male connector with the female connector and also to prevent the male connector from moving in at least one direction relative to the female connector.

41. A connector as in claim 1, further comprising a protective sheath adapted to cover the male and female connectors.

42. A connector as in claim 1, wherein the connector has a diameter less than or substantially similar to a diameter of the neurological device.

43. A connector as in claim 1, wherein the connector has a diameter sized to facilitate subcutaneous implantation with a guide tube or tunneler.

44. A connector as in claim 1, wherein the connector is substantially symmetrical about an axis or a plane.

\* \* \* \* \*